United States Patent [19]

Gay

[11] Patent Number: 4,509,855
[45] Date of Patent: Apr. 9, 1985

[54] DUAL LIQUID AND GAS CHROMATOGRAPH SYSTEM

[75] Inventor: Don D. Gay, Aiken, S.C.

[73] Assignee: The United States of America as represented by the United States Department of Energy, Washington, D.C.

[21] Appl. No.: 464,840

[22] Filed: Feb. 8, 1983

Related U.S. Application Data

[63] Continuation-in-part of Ser. No. 407,538, Aug. 12, 1982, Pat. No. 4,470,699.

[51] Int. Cl.³ ............................................. G01N 21/73
[52] U.S. Cl. ....................................... 356/72; 356/316
[58] Field of Search ........................... 356/72, 73, 316; 73/23.1, 61.1 C

[56] References Cited

U.S. PATENT DOCUMENTS 3,612,686 10/1971 Braman et al. .................. 356/316 X

OTHER PUBLICATIONS

Carnahan et al., *Anal. Chimica Acta*, 130, (2), Oct. 1981, pp. 227-241.
Wasik et al., *J. Chromatog. Sci*, vol. 18, Dec. 1980, pp. 660-663.
Lloyd et al., *Anal. Chem.* vol. 50, No. 14, Dec. 1978, pp. 2025-2029.
Layman et al., *Anal. Chem.*, vol. 53, No. 4, Apr. 1981, pp. 747-748.
Young, *J. Chromatography*, vol. 21, No. 2, Sep. 1981, pp. 197-201.
Broerman et al., *J. Chromatog Sci*, vol. 19, Oct. 1981, pp. 508-513.
McGuffin et al., *J. Chromatography*, vol. 218, Nov. 1981, pp. 179-187.

Primary Examiner—F. L. Evans
Attorney, Agent, or Firm—Allen F. Westerdahl

[57] ABSTRACT

A chromatographic system that utilizes one detection system for gas chromatographic and micro-liquid chromatographic determinations. The detection system is a direct-current, atmospheric-pressure, helium plasma emission spectrometer. The detector utilizes a non-transparent plasma source unit which contains the plasma region and two side-arms which receive effluents from the micro-liquid chromatograph and the gas chromatograph. The dual nature of this chromatographic system offers: (1) extreme flexibility in the samples to be examined; (2) extremely low sensitivity; (3) element selectivity; (4) long-term stability; (5) direct correlation of data from the liquid and gas samples; (6) simpler operation than with individual liquid and gas chromatographs, each with different detection systems; and (7) cheaper than a commercial liquid chromatograph and a gas chromatograph.

8 Claims, 7 Drawing Figures

DUAL LIQUID AND GAS CHROMATOGRAPH SYSTEM

The United States Government has rights in this invention pursuant to Contract No. DE-AC09-76SR00001 between the U.S. Department of Energy and E. I. DuPont de Nemours & Co.

This is a continuation-in-part of U.S. application Ser. No. 407,538, filed on Aug. 12, 1982, entitled "Micro-Column Plasma Emission Liquid Chromatograph", now U.S. Pat. No. 4,470,699.

BACKGROUND OF THE INVENTION

1. Field of the Invention and Contract Statement

The invention relates to direct current plasma emission spectrometers for use in combination with microcolumn liquid and gas chromatographs.

2. Discussion of Background and Prior Art

Chromatography is a physical method of separation, in which the components to be separated are distributed between two phases; one of these phases constituting a stationary bed of large surface area, and the other being a fluid that percolates through or along the stationary bed. The stationary phase can be either a solid or a liquid, and the moving phase may be either a liquid or a gas. All of the known types of chromatography broadly fall into four categories, namely liquid-solid, gas-solid, liquid-liquid, and gas-liquid. In all of the known chromatographic techniques, the solutes to be separated migrate along a column (or, as in paper or thin layer chromatography, the physical equivalent of a column), and of course the basis of the separation lies in different rates of migrations for the different solutes. The rate of migration of a solute is the result of two factors, one tending to move the solute and the other to retard it.

Liquid chromatography (LC) is a rapidly expanding analytical technique for the separation of chemical compounds which have low or non-existent vapor pressures and are water soluble. The conventional detection systems for liquid chromatography are based on the refractive indices, absorption, fluorescent or electrochemical properties of the compounds in question. Such detectors do not offer selectively or sensitivity of the magnitude provided by detectors for gas chromatograpy.

Micro-column liquid chromatographic systems are currently in the infancy of the state-of-the-art development of liquid chromatography. Three basic nomenclatures define micro-column liquid chromatography: (1) open tubular liquid chromatography; (2) microbore liquid chromatography; and (3) capillary liquid chromatography. Inherent with all three designs are (a) extremely high theoretical plate separations, (b) high mass sensitivities and (c) extremely low solvent flow rates (1 to 5 ml/min. as compared to 40 to 100 ml/min. for conventional liquid chromatographs).

In plasma emission spectroscopy, injection of liquid samples, and of effluent fluids from a chromatographic column, into the plasma space of a source are known. One of the problems before has always been how to get rid of the excess solvent before it hits the plasma region. Conventional flow rates do not allow an excited plasma state to remain in effect. The use of microcolumns in liquid chromatography provides a reduction in solvent flow rate.

SUMMARY OF THE INVENTION

An object of the invention is to provide an improved detection system for a dual liquid- and gas-chromatography. Other objects and advantages of the invention are set out herein or are obvious herefrom to one ordinarily skilled in the art.

The objects and advantages of this invention are achieved by the improved detection system of the invention.

To achieve the foregoing and other objects and in accordance with the purpose of the invention, as embodied and broadly described herein, the invention involves a dual mode direct current plasma spectrometer. Such spectrometer includes a plasma source unit which includes (i) a plasma source, (ii) eluant and gas inlet means, (iii) a plasma sustaining region, and (iv) a plasma viewing means in the region connected to the spectrometer. A micro-column liquid chromatograph is connected to the eluant inlet means, and a gas chromatograph is connected to the gas inlet means. Heater means is attached to the plasma source unit, and is adapted to control the temperature of the eluants from both chromatographs to the plasma region.

The invention also involves, in a direct current plasma emission spectrometer, which includes a plasma source unit and a micro-column liquid chromatograph, the improvement which includes gas inlet means disposed in the plasma source unit. Gas chromatograph means is connected to the plasma source unit through the gas inlet means. Heater means is attached to the plasma source unit, and is adapted to control the temperature of the eluant from the gas chromatograph.

The invention further involves, in a direct current plasma emission spectrometer, which includes a plasma source unit having a carrier gas therein and a source of electrical potential to sustain a plasma, and a micro-column liquid chromatograph connected to an inlet of the plasma source unit, the improvement which includes a gas inlet means disposed in fixed spaced relation to the liquid chromatograph inlet. A liquid chromatograph means is connected to the plasma source unit through the eluant inlet means, and a gas chromatograph means is connected to the plasma source unit through the gas inlet means. A heater means surrounds the inlets of the plasma source unit, and is adapted to control the temperature of the plasma and the vapor phase from both chromatographs.

The spectrometer of the invention is operable in a liquid chromatograph mode or in a gas chromatograph mode.

The pertinent parts of U.S. application Ser. No. 407,538, inventor: Don Douglas Gay, filed on Aug. 12, 1982, entitled "Micro-Column Plasma Emission Liquid Chromatograph," are incorporated herein by reference. Such application discloses an improved source unit for use in a direct current plasma emission spectrometer in combination with a micro-column liquid chromatograph. The plasma source unit includes a quartz capillary tube having an inlet means, outlet off gas means and a pair of spaced electrodes defining a plasma region in the tube. The inlet means is connected to and adapted to receive eluant of the liquid chromatograph along with a stream of plasma-forming gas. There is an opening through the wall of the capillary tube penetrating into the plasma region. A soft glass capillary light pipe is disposed at the opening, is connected to the spectrometer, and is adapted to transmit light passing from the plasma region to the spectrometer. There is also a source of electromotive force connected to the electrodes sufficient to initiate and sustain a plasma in the plasma region of the tube.

The invention system uses parts of the microcolumn plasma emission liquid chromatograph of U.S. application Ser. No. 407,538 as a portion of the invention dual chromatograph and expands and improves on it making a more universal analytical instrument.

The heart of the invention dual instrument is the central detection system, the direct current, atmospheric pressure, helium plasma emission spectrometer, which, in turn, is based upon the plasma source unit. For the micro-column plasma emission liquid chromatograph (of U.S. application Ser. No. 407,538), the liquid effluent from the micro-column is directed into a special side-arm below the electrode arms, between which the plasma is compartmentalized. In the invention instrument, another side-arm is attached to the central axis below the liquid chromatograph (LC) effluent to receive the gaseous effluent from the gas chromatograph (GC) column. The gas chromatograph side-arm is positioned below the liquid chromatograph side-arm to prevent any residual liquid chromatograph effluent from becoming entrained or absorbed in the gas chromatograph side-arm.

With either mode of operation, as a liquid chromatograph or a gas chromatograph, the helium carrier gas-flow through the plasma source unit central axis to sustain the plasma is maintained. In addition, in the gas chromatograph mode of operation, helium is used as the inert carrier gas through the gas chromatograph column. A gas splitter valve is employed in the gas chromatograph mode to divert a small quantity of helium from the central axis through the gas chromatograph column and back into the central axis via the gas chromatograph side-arm. The configuration and stability of the plasma is not affected.

Some of the advantages of micro-column plasma emission dual liquid- and gas-chromatography of the invention detector over conventional and commercially available liquid chromatographs and gas chromatographs are:

(1) One detection system for two chromatographic systems:
  (a) This allows for more reliable data because calibration and standardization techniques and procedures are minimized.
  (b) The operator or potential operator can more easily learn the procedures for one system than for many as with absorbance, fluorescence and refractive index detector components for a liquid chromatograph or electron capture, flame ionization and thermal conductivity detector components for a gas chromatograph.
  (c) The interpretation and correlation of data is much easier with only one detection system.
  (d) Less physical space is needed than for two conventional chromatographs.
  (e) The cost is reduced.
(2) Increased flexibility. A wide range of sample preparations can be employed to separate the compound in question from others.
(3) Increased sensitivity. Atomic emission (which the invention uses) is superior in sensitivity to absorbance, fluorescence, electrochemical or refractive index detectors currently employed as detection devices for liquid chromatographs and is superior in sensitivity to thermal conductivity, flame ionization or electron capture detectors currently employed as detection devices for gas chromatography.
(4) Increased selectivity. The plasma emission detector is element specific and selective. Each element emits characteristic wavelengths of light. This detector capitalizes upon that by being continuously tunable to various wavelengths of interest.
(5) Increased strength and less fragility of the Plasma Source Unit. Because only a portion of the plasma is used and it is viewed directly through the viewing port via the light pipe, the plasma source unit does not have to be transparent or quartz, i.e., to let ultraviolet wavelengths through, (but can be). The plasma source unit can be a ceramic material or alumina oxide or some other high melting material rather than quartz. This will provide more strength and less fragility of the plasma source unit.
(6) Increased stability. Problems with etching, solvent polymerization and carbon formation on the walls of conventional quartz plasma source units encountered by other detectors are eliminated with the invention detector. The sensitivity of other plasma source units is deleteriously affected by wall etching due to high temperatures, solvent polymerization and carbon formation on the walls, but the invention detector is not affected by these problems.
(7) Very high signal to noise ratio. Such is accomplished by the invention by selectively looking at the most reactive region of the plasma rather than the entire plasma. Such feature is unique to the invention detector. The invention detector looks at a fraction of the total plasma rather than the entire plasma as in other plasma detectors. The fraction utilized is the region giving the greatest elemental emission signal. Therefore, this signal response is not diluted or averaged over the entire plasma and a greater response is obtained.
(8) Increased power in separating similar chemical species. The micro-column approach for liquid chromatography (LC) and the capillary column approach for gas chromatography (GC) offer a greater number of theoretical plates for separation efficiency and a higher mass sensitivity than conventional liquid chromatograph or gas chromatograph columns. The power of a liquid chromatograph or gas chromatograph column in separating compounds is based upon the number of theoretical plates available in the column. The greater the number of theoretical plates, the more power that is available to distinctly separate chemically-similar compounds.
(9) Less expensive. This instrument is less expensive than buying two commercial chromatographs offering their most sensitive detection systems. No commercial detector compares with the invention plasma emission system for sensitivity, selectivity, and stability.

Analytical chromatography has developed into a primary means of easily determining specific chemical compounds in a matrix containing many compounds. Gas chromatography has developed faster than liquid chromatography because sensitive detectors have been developed for it. However, new detectors for liquid chromatography are being developed which give more senstivity than conventional detectors, although the new sensitivities do not equal those given by gas chromatograph detectors, with the exception of the direct current atmospheric pressure helium plasma emission spectrometer as developed in U.S. application Ser. No. 407,538 and further developed herein. The capillary and micro-columns developed for gas chromatography and liquid chromatography in the invention system increase the separation powers of either chromatographic system, aiding in the increase in sensitivity.

One specific area of use for the invention instrument is in the field of preventive medicine. Health facilities with a large number of recurring patients (e.g., public and private health clinics, hospitals, medical schools and associated hospitals, and large corporations) would benefit from the use of the invention instrument. The relative ease of operation and the adaptability of this instrument to new, divergent applications and techniques offer the potential for many more tests being done on an individual than that which is currently practiced at very little extra expense.

Current standard practice with diagnostic tests is to compare the level of a measured entity with the range of normal values in the population. By running samples through the instrument taken when individuals are healthy as well as sick and storing the information in a computer or on tape, the health facility could report the values of measured entities for a given test and date in relation to the normal values of the individual, rather than the population values. All body fluids and gases could be examined each time. By having both liquid chromatographic and gas chromatographic capabilities, volatile components as well as very low levels of water soluble components can be detected.

Also, the overall patterns for each chromatogram obtained for the tests would be examined for unexpected increases, decreases or appearance of new peaks when a disease process is encountered. This would significantly enhance the field of preventive medicine.

The invention dual liquid- and gas-chromatograph offers, for the first time, the ability to determine chemical compounds present in almost all matrices possible, regardless of vapor pressures. This instrument has broad applications in all research labs, private, academic or federal. Any aspect of research interest from air sampling to water sampling to the unraveling of complex biochemical metabolic pathways in plants, animals, micro-organisms and human systems can benefit from the sensitivity and element selectivity offered by the invention instrument. The wide linear range of response to concentration makes this instrument ideal for gross, preliminary examinations as well as for determining ultra-trace levels of elements or chemical compounds present anywhere. The cost is less than conventional highly sensitive liquid and gas chromatographic systems and takes up less space in a laboratory.

The detection system for liquid chromatography portion of the invention gives elemental selectivity as well as has 100 to 1000 times more sensitivity than current liquid chromatography detectors. The invention detector is an atmospheric-pressure direct-current helium-plasma emission spectrometer. When coupled to a micro-column liquid chromatograph, sensitivity and selectivity can be significantly gained for liquid chromatography.

Preferably the plasma-forming gas is helium, also, preferably the opening on the side of the capillary tube is between about 1 and 2 mm diameter. The capillary light pipe preferably has highly-polished internal walls.

Further, preferably the capillary light has a diameter between about 2 mm and 3 mm, and is disposed to maintain a gap of about 1 to 2 mm between the light pipe and the opening in the capillary tube. The invention dual system has much better selectivity and sensitivity than the prior art detectors.

Reference will now be made in detail to the present preferred embodiments of the invention, examples of which are illustrated in the accompanying drawing.

A BRIEF DESCRIPTION OF THE INVENTION

The accompanying drawings, which are incorporated in and form a part of the specification, illustrate the invention and, together with the description, serve to explain the principles of the invention. In the drawings.

DETAILED DESCRIPTION OF THE INVENTION

All parts, percentages ratios and proportions are on a weight basis unless otherwise stated herein or obvious herefrom to one ordinarily skilled in the art.

Figure 1:
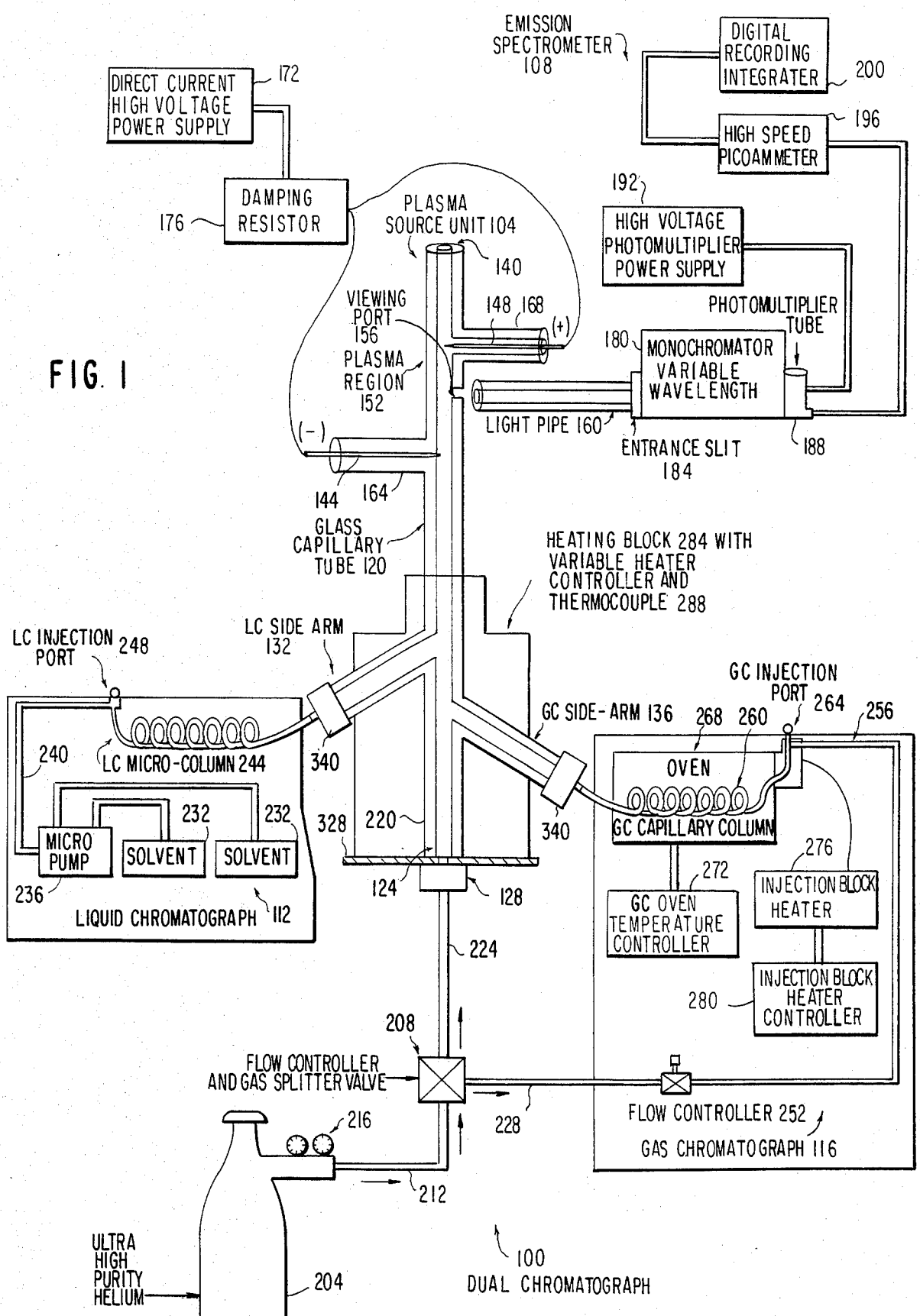
FIG. 1 is a schematic diagram of the system of the invention.
Figure 2:
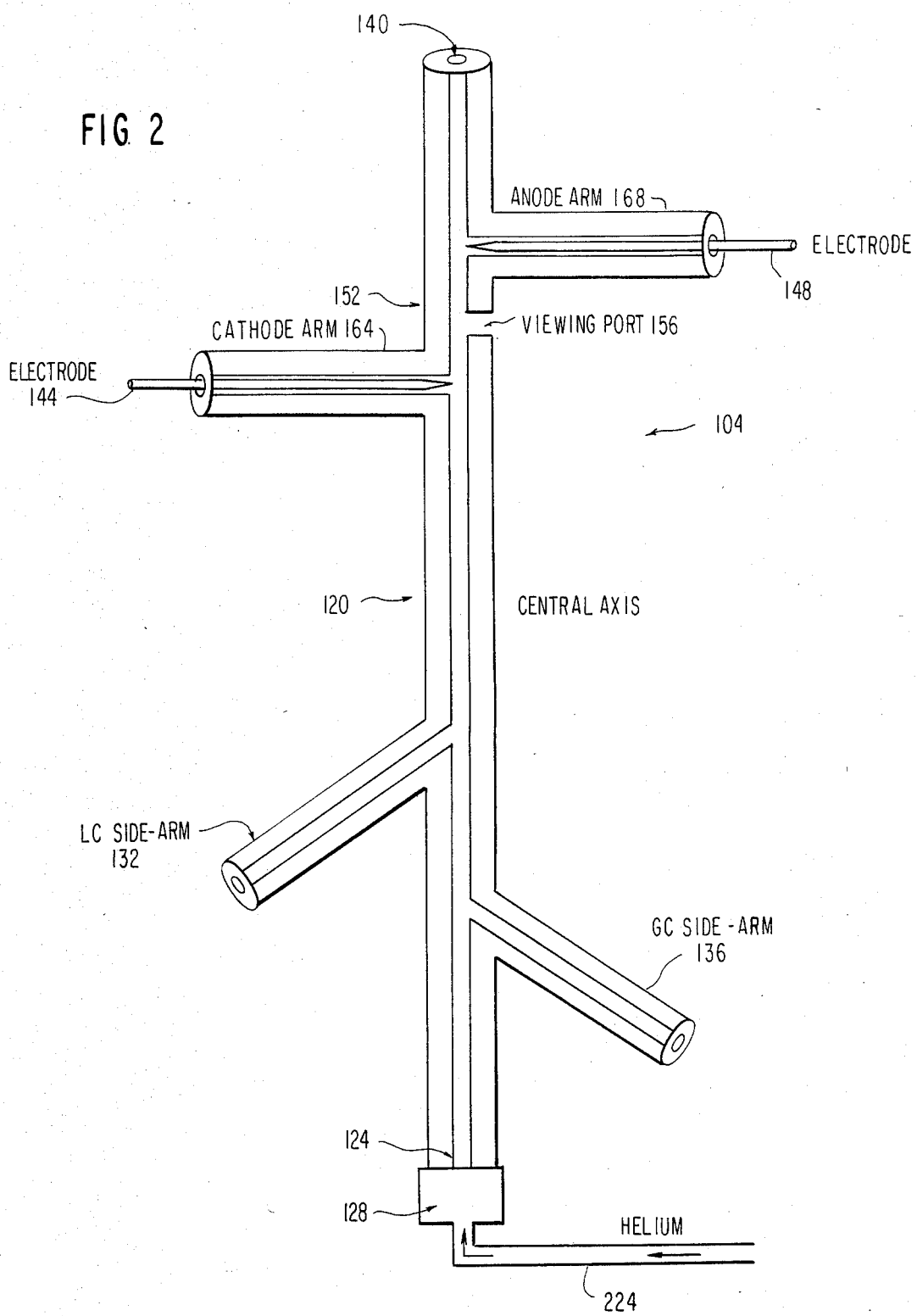
FIG. 2 is an elevational view of the plasma source unit of the system of FIG. 1.

Referring to FIG. 1, a preferred embodiment is disclosed which shows a schematic of dual liquid- and gas-chromatograph 100. Plasma source unit 104 is coupled with emission spectrometer 108, micro-column liquid chromatograph 112 and micro-column gas chromatograph 116. Plasma source unit 104 includes a glass capillary tube 120 having inlet 124 for receiving a stream of plasma-forming gas from connector 128, liquid chromatograph (LC) side arm 132, gas chromatograph (GC) side arm 136 and outlet off-gas means 140. Electrode (cathode) 144 positioned in cathode arm 164 and electrode (anode) 148 positioned in anode arm 168 define plasma region 152. See FIG. 2. Opening (viewing port) 156 in the wall of capillary tube 120 penetrates into plasma region 152. One end of soft glass capillary light pipe 160 is disposed at opening 156 and the other end thereof is connected to spectrometer 108 to transmit light to it from plasma region 152. GC side arm 136 is positioned closer to inlet 124 than LC side arm 132. Basically, the invention is a new analytical approach to dual liquid- and gas-chromatography combining micro-column gas chromatograph 116 and micro-column liquid chromatograph 112 with direct current plasma emission spectrometric detector 104, 108.

Ultra high pure (U.H.P.) helium from pressurized tank 204 flows into flow-controller-and-gas-splitter valve 208 via line 212 and is regulated by valves 216.

Part of the helium flow is directed into lower end 220 of inlet 124 via line 224. The other part of the helium flow is directed into gas chromatograph 116 via line 228.

Micro-column liquid chromatograph 112 includes solvent containers 232 connected to micro-pump 236, which in turn is connected by line 240 to coiled, micro-column 244. Liquid-chromatograph injection port 248 is situated in line 240 betweeen micro-pump 236 and micro-column 244. One end of micro-column 244 is connected to LC side arm 132 of capillary tube 120. Chromatograph solvent is forced into line 240 by means of micro-pump 236 and is transported to capillary tube 120 via LC micro-column 244 and LC side arm 132. Sample is injected into LC injection port 248 and is transported, along with the solvent from line 240, to capillary tube 120 via micro-column 244 and side arm 132.

LC side arm 132 is attached to the central portion of capillary tube 120 just below plasma region 152. The attachment region of side arm 132 is very narrow and serves as a nebulizer or atomizer. This is the preferred version of the nebulizer. Alternatively, the nebulizer of U.S. Pat. No. 3,958,883 are incorporated herein by reference. Another method for attaining the atomization required is given is Krien et al., "Application of Microbore Columns to Liquid Chromatography-Mass Spectrometry", Journal of Chromatography 251(2), 129–139, (1982), the pertinent parts of which are incorporated herein by reference. See the diagram on bottom of page 131 of Krien et al. The same thing they have done with the 0.5u porosity filter in the micro-column end, covered by a porous diaphram works very well in the system shown in FIG. 1 by inserting the covered and filtered micro-column end into LC side arm 132 up to the junction with the central portion of capillary tube 120. The eluant from the micro-column having the porosity filter and diaphragm emerges as a fine spray into the helium gas stream and is further atomized in it as it passes to the electrode plasma region 152. Heating the region between LC side arm 132 and cathode 144 facilitates a better combination of eluant and helium hitting the plasma. Alternatively, the scheme of Dedieu et al., "Application of a Combined Liquid-Chromatography", 251(2), 202–213, (1982). the pertinent parts of which are incorporated herein by reference, can be used. Dedieu et al. teaches a high-speed direct liquid introduction device as diagrammed at the bottom of page 207 therein. The end of the micro-column (termed "LC probe" in the diagram) can be fitted with the small "heated chambers" configuration as depicted and the entire structure inserted into LC side arm 132 up to the junction with the central portion of capillary tube 120. Also, the scheme of Schafer et al., "Direct Coupling of a Micro-High Performance Liquid Chromatograph and a Mass spectrometer", Jour. Chromatography 206(2), 245–252 (1981), the pertinent parts of which are incorporated herein by reference, can be used. In Schafer et al. the effluent from the micro-column (termed capillary in Schafer et al.) goes directly into the helium gas stream without a special nebulizer. This is similar to the preferred version of the nebulizer set out above.

The atomized eluant from the nebulizer region passes from LC side arm 132 into the helium gas stream in the central region of capillary tube 120. This mixture of helium and atomized eluant then passes into plasma region 152 between electrodes 144 and 148.

LC micro-column 244 separates the chemical compounds on the basis of chemical properties. The detection of the compounds on the basis of the emission spectrum of the element selected for monitoring is determined via variable wavelength monochromator 180.

A helium plasma is maintained after initiation with at least a 95 percent concentration of helium in plasma region 152. With less than 95 percent helium, the plasma is extinguished. The helium carrier gas flow rate normally used is 50 to 200 ml/min. The micro-column (244) flow rate of the solvent is 1 to 10 ul/min. With a 22-fold increase in volume when the liquid solvent is converted to a gas, the concentration of helium in plasma region 152 with a 50 ml/min. helium flow rate and 1 ul/min. effluent flow from micro-column 244 is 99.9 percent. Increasing the effluent flow to 10 ul/min. gives a helium concentration in plasma region 152 of 99 percent; the helium plasma is not extinguished.

Any suitable or conventional solvent, such as, acetonitrile-water, methanol-water, methanol, n-hexane-methanol-dichloromethane, acetonitrile-hexane, isopropanol-hexane, and n-hexane-methanol, can be used.

Micro-column gas chromatograph 116 includes helium line 228 connected to flow controller 252, which in turn is connected to helium line 256. Helium line 256 is also connected to coiled micro-column (capillary) column 260. The helium is used as a carrier gas. Injection port 264 is situated in line 256 between flow controller 252 and micro-column 260. One end of micro-column 260 is connected to gas chromatograph side arm 136 of capillary tube 120. Sample is injected into gas chromatograph injection port 264 and is transported, along with the helium from line 256, to capillary tube 120 via micro-column 260 and side arm 136.

Gas chromatograph side arm 136 is positioned below liquid chromatograph side arm 132 in order to prevent any residual liquid chromatograph effluent from becoming entrained or absorbed in gas chromatograph side arm 136.

Gas chromatograph portion 116 of the dual chromatograph 100 also includes oven 268 (having a temperature programmer 272), and injection port 264, which has injection block heater 276 and variable temperature controller 280.

Figure 3:
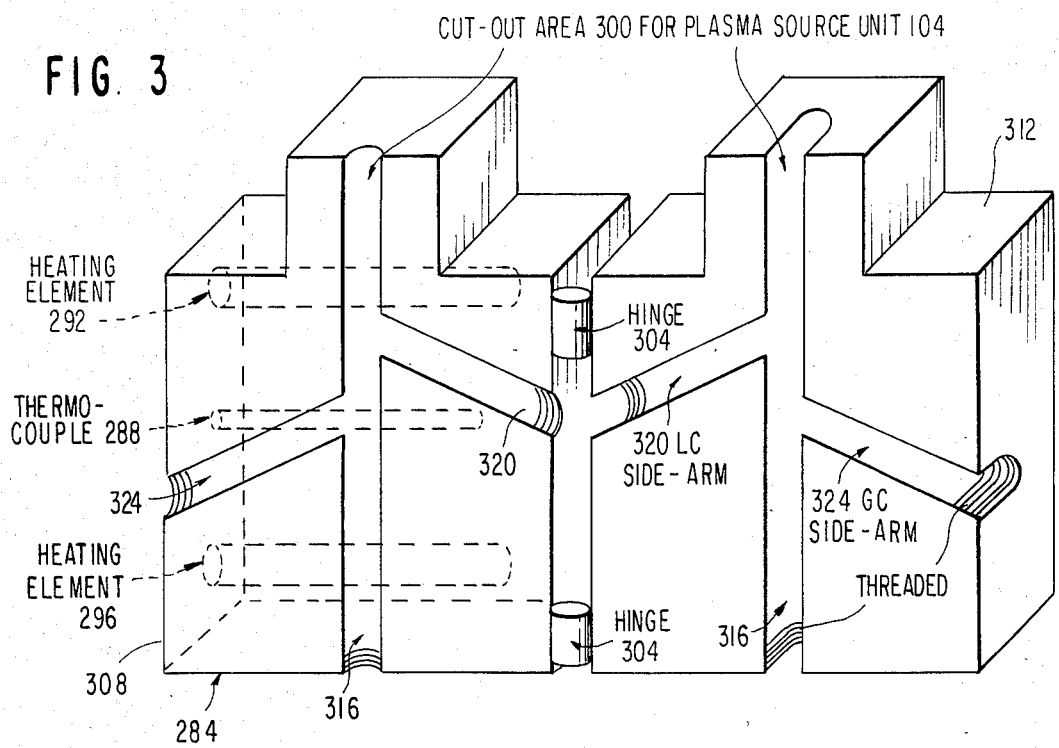
FIG. 3 is an elevational view of the heating element, in open position, for the plasma source unit of the system of FIG. 1.
Figure 4:
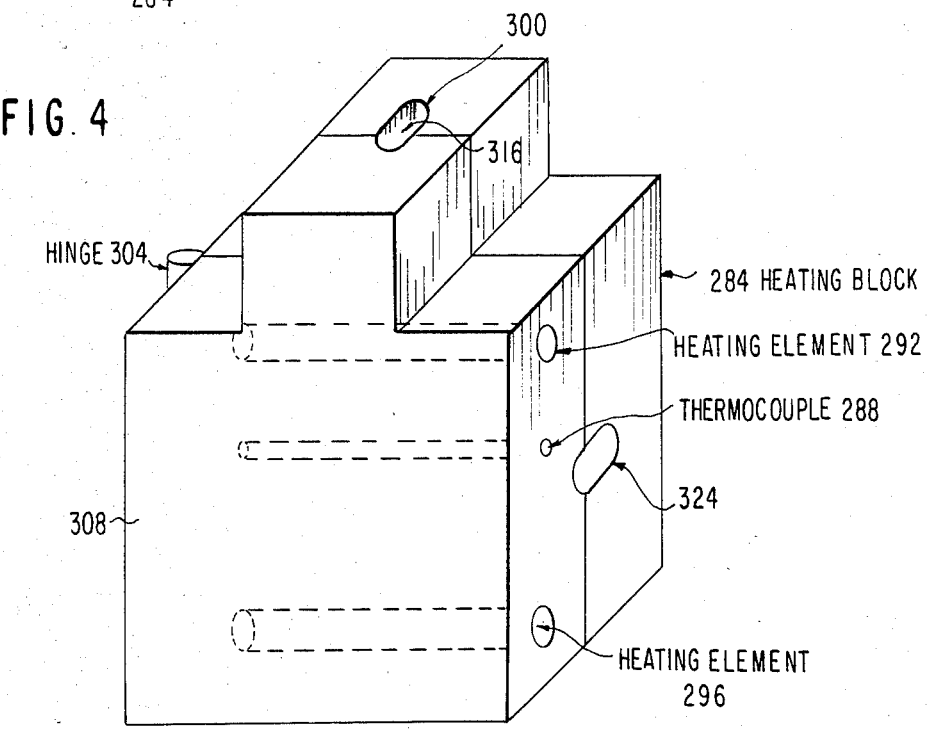
FIG. 4 is an elevational view of the heating element, in closed position, for the plasma source unit of the system of FIG. 1.
Figure 5:
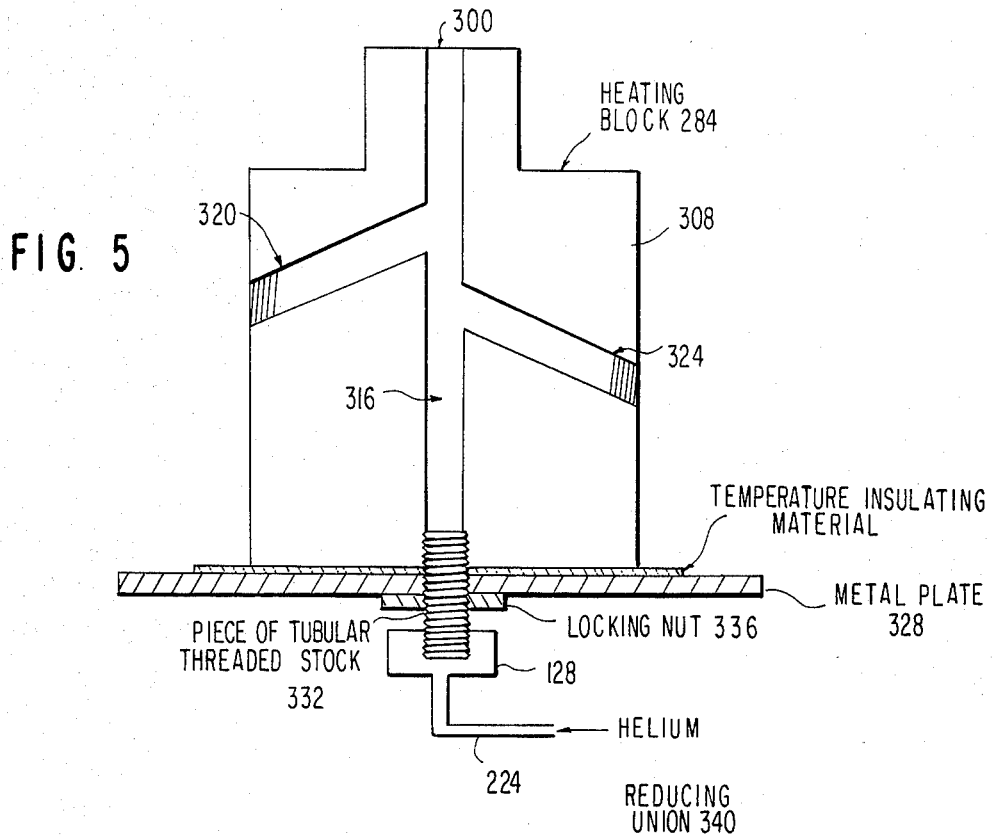
FIG. 5 is a vertical view of the anchoring mechanism for the heating block of the heating element of FIG. 3.

For attachment of gas chromatograph 116 to plasma source unit 104 via GC side-arm 136 requires an additional component, heating block 284 and variable temperature controller for plasma source unit 104. (See FIGS. 3 and 4.) Heating block 284 has front segment 308 and back segment 312, which are hinged (304) together. Mating cut-out areas 300 in front and back segments 308, 312 each have main passageway 316, LC side-arm passageway 320 and GC side-arm passageway 324. The entrance ends of passageways 316, 320, 324 are internally threaded. LC side arm 132, GC side arm 136 and the lower end of capillary tube 120 fit within cutaway area 300 of heating block 284. In the GC mode various temperatures above ambient are used in GC oven 260 to effectively separate compounds in the column 260. In order to sustain the vapor phase of the compounds from column 260 to plasma region 152 and to avoid condensation along the path, plasma source unit heating block 284 maintains the temperature attained in oven 268 into the plasma region 152. Thermocouple 288 is inserted into heating block 284 to monitor the temperature. Heating block contains heating elements 292, 296. Heating block 284 also allows plasma source unit 104 to be anchored to metal plate 328 to provide rigidity and small threaded section at the base of plasma source unit cut-out 300. A piece of tubular threaded stock 332 fits into heating block 284 through which the basal portion of plasma source unit 104 fits. Locking nut 336 anchors heating block 284 to metal plate 328. The lower end of tubular threaded stock 332 is threaded into internally-threaded connector 128. A sheet of temperature insulating material is positioned between metal plate 328 and heating block 284.

Figure 6:
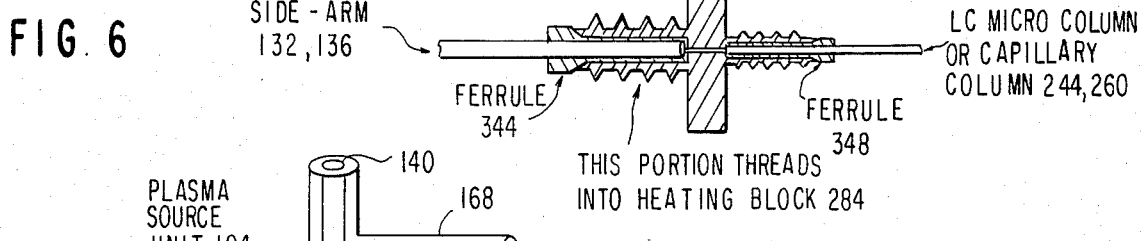
FIG. 6 is partial cross-sectional longitudinal view of the coupling mechanism of the micro and capillary columns to the liquid-chromatograph and gas-chromatograph side-arms of the system of FIG. 1.

Rigidity and strength are also supplied to the LC and GC side-arms 132, 136 through the use of heating block 284. Threaded portions at the outlet ends of each side-arm (132, 136) allow for reducing union 340 to be inserted in each outlet end. (See FIG. 6.) LC and GC side-arms 132, 136 of plasma source unit 104 fit into reducing unions 340 and are made gas tight (leak proof) by means of ferrules 344, 348. This effectively anchors each side-arm 132, 136, providing rigidity to it. In addition, reducing union 340 provides an excellent means by which to couple capillary 260 and micro-columns 244 to side-arms 132, 136 with a minimum amount of dead space in the system. This minimizes peak broadening and associated signal reduction. Having all of this in heating block 284 guarantees the passage of already separated chemical compounds via the micro-column 244 or capillary column 240 into plasma region 152 for quantitation.

The LC mode of operation also benefits from heating block 284 around plasma source unit 104. The effluent from LC micro-column 244 is atomized through nebulization techniques before it is swept into plasma region 152. This atomization is significantly enhanced when the effluent is heated.

The best operation in the gas chromatograph mode is with capillary columns rather than with conventional large bore columns because the heating of large bore columns to attain the chromatographic parameters required for adequate separation in short time periods introduces a phenomenon termed "column bleed" into the detection system. Such "bleed" is the thermal desorption of small amounts of organic phases coated to the diatomaceous earth or silica gel stationary material packed in the column. In the invention dual chromatograph, such column bleed is sufficient at higher temperatures (generally over 100° C.) to distort the baseline, thus causing a loss of sensitivity. The capillary columns offer greater abilities to separate closely related compounds than do conventional large bore columns. Also, the amount of "column bleed" does not deleteriously affect the sensitivity.

Direct current high voltage power source 172 is electrically connected to electrodes 144 and 148 with intermediate damping resistor 176. The noted end of light pipe 160 includes monochromator 180, photomultiplier tube 188, high-voltage photomultiplier power source 192, high-speed picoammeter 196, which is electrically connected to photomultiplier tube 188, and digital recording integrator 200, which is electrically connected to picoammeter 196.

Plasma source unit 104 has quartz capillary tube 120 through which helium gas is forced between two electrodes 144 and 148. The plasma, or region of excitation, 152 occurs between electrodes 144 and 148. conventional plasma source units have a contained region for the plasma. The emitted light passes through the quartz capillary walls, through a quartz lens (or reflected by highly polished mirrors) into a variable wavelength monochromator entrance slit or through special filters. The selected wavelengths impringe upon a photmultiplier tube which changes light energy into electrical impulses.

Plasma source unit 104 has a specific region (152) for plasma excitation. However, a very small diameter hole 156, termed the "viewing port", is drilled through one wall of quartz capillary tube 120 near cathode 144. Instead of a conventional quartz lens or mirror, the invention uses a piece of soft glass capillary tubing 160 having highly polished internal walls to focus the light emitted from the plasma into entrance slit 184 of variable-wavelength monochromator 180. Soft glass capillary tube 160 is termed a "light pipe." The emitted light from the highly energetic helium plasma (152) is transmitted directly into monochromator 180 through entrance slit 184.

One serious problem with conventional contained quartz plasma units is that signal deterioration occurs almost immediately with the use of a new quartz capillary tube. Etching of the quartz walls occurs rapidly because the temperature of the plasma is 3000° to 5000° C. Such etching allows less and less light to be transmitted through the walls into the monochromator and photomultiplier tube. Also, solvent polymerization and carbon buildup on the internal walls of the quartz capillary tube necessitate frequent cleanings to let the emission light pass through. With the use of quartz lenses or mirrors as focusing devices, almost all (if not all) of the plasma region is focused onto the entrance slit of the monochromator. Various studies have shown that all regions of the plasma do not cause equal light emissions from elements under investigation.

Plasma source unit 104, which can be a quartz fabrication, can easily be another high melting material, i.e., ceramic or a metallic oxide. Plasma source unit 104 does not have to be transparent to allow emitted light wavelengths into monochromator 180 for separation and subsequently into photomultiplier tube 188 for quantitation. Plasma source unit 104 has a 1 mm hole drilled into internal capillary 120 and is termed viewing port 156. Port 156 is positioned 2 to 3 mm above cathode 144, the lower electrode, because most elemental emissions are strongest in this region, as opposed to regions closer to anode 148. Instead of focusing all of the plasma onto entrance slit 184 of the monochromator 180 by lens or mirror systems of conventional systems, the plasma at viewing port 156 is channeled into the monochromator via a soft glass, 2 to 3 mm internal diameter capillary tube 160, termed light pipe 160. Maximum efficiency of light transfer occurs with light pipe 160 which has ground and polished internal surfaces. Light pipe 160 needs to be between 6 to 15 inches long for maximum light transfer. The small angle provided for the light transfer allows almost all of the light from the plasma to be reflected off the internal walls of light pipe 160 and into monochromator 180.

The advantages of using viewing port 156 and light pipe 160 over conventional methodologies are that: (1) the emitted light passes totally unrestricted from the plasma to monochromator 180; (2) the signal to noise ratio is very high: (3) no signal deterioration occurs because of the plasma; (4) although carbon or polymer formation may occur on inner capillary (120) walls of source unit 104, a longer functioning lifetime; and (5) plasma source unit 104 does not have to be transparent or quartz because of viewing port 156 into the plasma.

Plasma source unit 104 effectively reduces or eliminates the problems associated with conventional plasma source units and focusing devices. Because "viewing port" 156 directly into the plasma (152) is used, etching of the quartz walls does not make any difference on the signal. The lift span and functionality of quartz plasma source unit 104 is 10 to 50 times greater (at least) than conventional source units. Solvent polymerization and carbon formation do occur in the invention unit, but signal degradation does not occur. Introduction of small quantities of oxygen into the helium flow reduces this carbon buildup. Lastly, by having "viewing port" 156 for most elements, and using glass "light pipe" 160 to transmit only the light from port 156 into monochromator 180, the highest signal to noise ratio can be obtained and maintained.

Helium is preferred over argon as the gas for the plasma, because it produces a higher temperature as a plasma and is more energetic than argon. Most applications using helium as a plasma source require the helium to be maintained under reduced pressure in order for a plasma to be initiated. With the invention system, a functional helium plasma is initiated and maintained at standard atmospheric pressure. The plasma is automatically initiated when the current and voltage applied to electrodes 144 and 148 reach a certain level. In order to make the invention system fully automatic in regard to plasma initiation, large damping resistor 176 is built into the electric lines to electrodes 144 and 148. The required settings for initiation can be maintained on the direct current power supply 172, so that if the plasma is extinguished by the passage of a large volume of solvent, the plasma will re-initiate itself once the solvent has passed.

Figure 7:
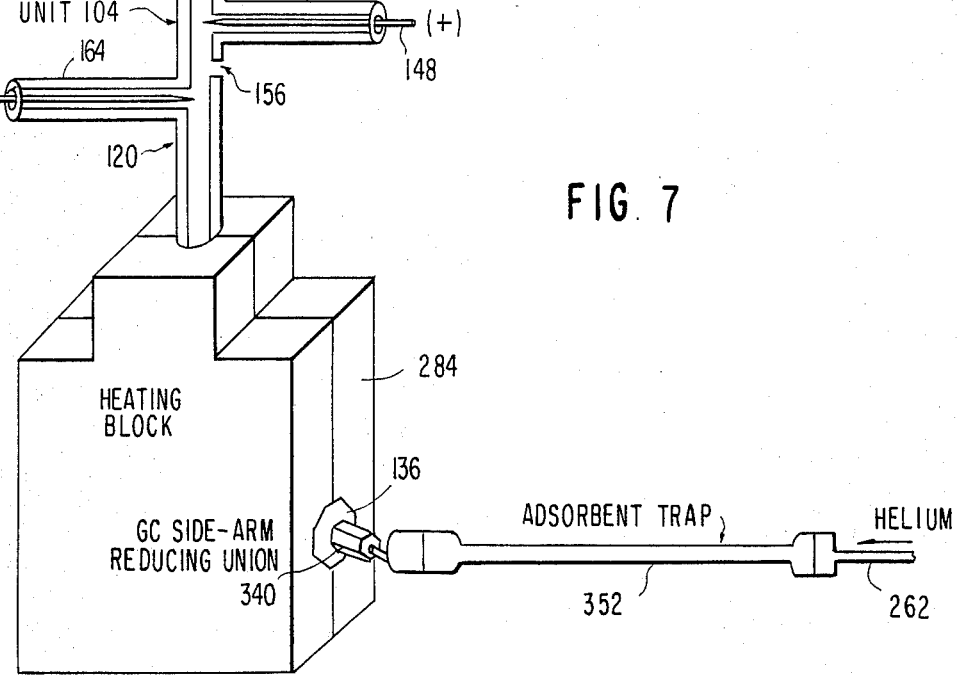
FIG. 7 is an elevational view of coupling special adsorbent traps for the liquid- and gas-chromatographs of the system of FIG. 1.

To be even more compatible with various types of samples to the analyzed, another feature is available with analytical system 100. Sometimes only one chemical compound in the environment is of interest. Special adsorption materials, particularly for air sampling, are available for many individual chemical compound that selectively adsorb the one for which it is designed and lets all others pass through. At a remote sampling site, large quantities of air can be drawn through this adsorbent and the chemical in question trapped. Generally, the adsorbent material is sequestered in either a stainless steel tube or glass column and the whole system is called a "trap" (352) or a "trapping system" (352). Traps 352 in the field are sealed and brought back to the lab for determination of the chemical in question via the dual chromatograph liquid and gas system 100. To make these determinations, GC capillary column 260 is uncoupled from GC side-arm 136 of plasma source unit 104 and one end of trap 352 is coupled to GC side-arm 136. (See FIG. 7.) The other end of trap 352 is coupled to the GC helium line (of column 260). In most applications, the trapped chemical can be thermally desorbed from the adsorbent, that is, by heating trap 352 to a desired temperature, the trapped chemical is released from the adsorbent and swept into plasma region 152 via the helium carrier gas. The element selective feature of detection system 100 allows extreme flexibility in the types of chemical compounds that can be determined.

Thermal desorption can be accomplished by wrapping each individual trap 352 with nichrome heating wire (not shown) and heating the wire via a variac rheostat (not shown) to a desired temperature. Also, a small oven or block heater (not shown) can be used in which trap 352 is placed, heated and desorbed. The length of the connections between trap 352 and GC side arm 136 need to be minimized to prevent peak spreading.

If several compounds of similar structure are of interest, rather than just one, instrument 100 can determine these as well. The compounds are adsorbed in trap 352 and trap 352 is attached to GC column 260 through injection port 264. The helium carrier gas is attached to the free end of trap 352 and using thermal desorption, the trapped compounds are swept into GC column 260, separated, identified by retention times and quantified in plasma region 152.

Similar methodologies can be conceived for use with the liquid chromatographic portion (112) of invention instrument 100. Various commercial traps or concentrating systems are available that allow for large volumes of water samples to passed through while collecting or retaining only a particular class of chemical compounds. Sampling can be done in the field and collecting devices brought back to the lab for analysis. Attaching the collector prior to micro-column 244 and pumping the solvent through the collector will desorb the trapped chemicals from the collector with the separation occurring in the micro-column 244 and quantitation occurring in plasma region 152.

The foregoing description of preferred embodiments of the invention has been presented for purposes of illustration and description. It is not intended to be exhaustive or to limit the invention to the precise form disclosed, and obviously many modifications and variations are possible in light of the above teachings. The embodiments were chosen and described in order to best explain the principles of the invention and its practical application to thereby enable one skilled in the art to best utilize the invention in various embodiments and with various modifications as are suited to the particular use contemplated. It is intended that the scope of the invention be defined by the claims appended hereto.

What is claimed is:

1. A dual mode direct current plasma spectrometer which comprises, in combination:
    (a) a plasma source unit including
        (i) a plasma source, (ii) eluant and gas inlet means, (iii) a plasma sustaining region, and (iv) a plasma viewing means in said region connected to said spectrometer;
    (b) a micro-column liquid chromatograph connected to said eluant inlet means;
    (c) a gas chromatograph connected to said gas inlet means; and
    (d) heater means attached to said plasma source unit, said heater means being adapted to control the temperature of said plasma and the vapor phase from said chromatographs (b) and (c).

2. The improvement as claimed in claim 1 wherein said plasma source is plasma-forming gas which is helium.

3. The improvement as claimed in claim 1 wherein the plasma viewing means is an opening in said plasma source unit.

4. The improvement as claimed in claim 3 wherein said opening is between about 1 and 2 mm diameter.

5. In a direct current plasma emission spectrometer, which includes a plasma source unit and micro-column liquid chromatograph, the improvement which comprises:
    (a) gas inlet means disposed in said plasma source unit;
    (b) gas chromatograph means connected to said plasma source unit through said gas inlet means; and (c) heater means attached to said plasma source unit, said heater means being adapted to control the temperature of the plasma and the vapor phase from said gas chromatograph.

6. The improvement as claimed in claim 5 wherein said spectrometer is operable in a liquid chromatograph mode or in a gas chromatograph mode.

7. In a direct current plasma emission spectrometer, which includes a plasma source unit having a carrier gas therein and a source of electrical potential to sustain a plasma, and a micro-column liquid chromatograph connected to an inlet of said plasma source unit, the improvement which comprises:

(a) a gas inlet means disposed in fixed spaced relation to said liquid chromatograph inlet;
(b) a gas chromatograph means connected to said plasma source unit through said gas inlet; and
(c) a heater means surrounding the inlets of said plasma source unit, said heater means being adapted to control the temperature of said plasma and the vapor phase from said chromatographs (b) and (c).

8. The improvement as claimed in claim 7 wherein said spectrometer is operable in a liquid chromatogaph mode or in a gas chromatograph mode.

* * * * *